Figure 1:
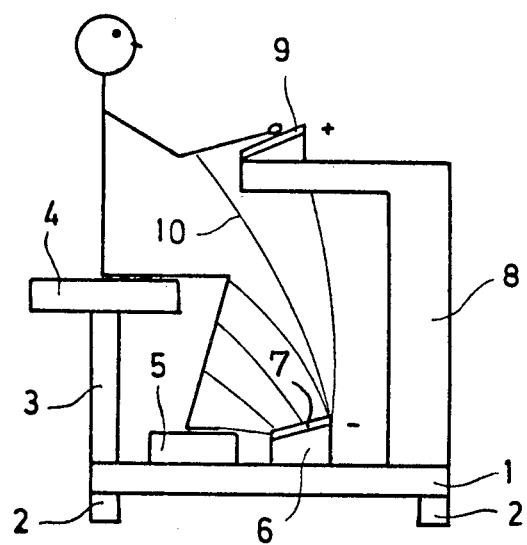

United States Patent [19]

Mandel

[11] 4,222,658
[45] Sep. 16, 1980

[54] DEVICE FOR APPLYING THE KIRLIAN PHOTOGRAPHY FOR DIAGNOSIS PURPOSES ON HUMAN BEINGS

[76] Inventor: P. Friedrich Mandel, Hildastrasse 13,, 7520 Bruchsal, Fed. Rep. of Germany

[21] Appl. No.: 965,916

[22] Filed: Dec. 4, 1978

[30] Foreign Application Priority Data

Dec. 5, 1977 [DE] Fed. Rep. of Germany ....... 2754031

[51] Int. Cl.³ ...................... G03B 19/00; G03B 41/00
[52] U.S. Cl. .................................. 354/354; 128/653; 354/3; 354/62
[58] Field of Search ............................ 354/3, 62, 354; 250/451, 456, 475, 324, 326, 526; 128/377, 378, 653, 665

[56] References Cited

PUBLICATIONS

Shawver, L. J., Science Focuses on a 'Light of Life', in Science News, vol. 104, No. 13, 9-29-73, pp. 202-204.

Primary Examiner—John Gonzales
Attorney, Agent, or Firm—Becker & Becker, Inc.

[57] ABSTRACT

A device for use in connection with Kirlian photography, which includes a seat insulated with regard to a support for the seat, a foot rest insulated relative to a support therefor and arranged at a level ahead of and below the seat, a bottom electrode arranged in spaced relationship to and ahead of the foot rest and insulated with regard to a support for the foot rest. The device, furthermore, comprises a plate electrode arranged above the bottom electrode and insulated with regard to the bottom electrode and the support for the plate electrode, the bottom electrode and the plate electrode being respectively connected to the poles of a high frequency generator.

3 Claims, 2 Drawing Figures

DEVICE FOR APPLYING THE KIRLIAN PHOTOGRAPHY FOR DIAGNOSIS PURPOSES ON HUMAN BEINGS

The present invention relates to a device for employing the Kirlian photography by means of a high frequency generator for diagnostic purposes on the human body.

Already 1939, the discoverers of the Kirlian photography, Mr. and Mrs. Kirlian, have studied the photography of spark discharges which by the employment of high frequency-high tension currents can be ascertained or identified on the human body. Kirlian himself describes this phenomenon as follows: "The basic principle of photography by means of high frequency currents is based on the transformation of non-electric properties of the photographed objects into electric properties by the movement in a field in which the controlled transfer of electric charges occurs from an object to a photographic film or fluorescent screen." Therefore, a prerequisite for the Kirlian photography is an electric field which, according to Kirlian, is formed between the capacitor plates which are operatively connected to the resonant or oscillating circuit of the high frequency generator. Therefore, according to Kirlian, the picture taking was always carried out in such a way that the object to be photographed was either with the interposition of a film or a fluorescent screen, placed between the two capacitor plates, or that the object to be photographed itself formed a pole of the high frequency oscillating circuit. However, Kirlian as well as his successors have always endeavored to avoid larger air gaps between the poles or capacitor plates which represent the end points of the high frequency oscillating circuit.

The Kirlian photography of live or dead objects has furnished a number of partially spectacular pictures which according to various scientists could be interpreted or evaluated as a picture of the respective "energy situation" of the photographed object. This finding has lead to attempts to employ the Kirlian photography as diagnostic means aiding in the recognition of conditions of disease in the human body.

In the meantime, scientists all over the world have experimented with the Kirlian photography without, however, realizing an advance with regard to the employment of the Kirlian photography as auxiliary means for diagnostic purposes. This failure is probably based not so much on the Kirlian photography itself as on the fact that the obtained results could not be reproduced. In the individual laboratories the Kirlian photography was practiced with different frequencies and voltages and with different picture taking situations. This was done particularly because the endeavor now as then aims at bringing the two ends of the oscillator resonant circuit of the high frequency generator as close as possible to the object to be exposed to light, which means, so far as the human being is concerned, to bring the two ends as close to the human body as possible. Generally this is done by connecting the human body to one pole of the oscillating circuit, whereas the other pole is connected to any desired type of electrode on which, through the interposition of a light sensitive foil or a fluorescent screen the object to be photographed, for instance a finger tip, is placed. As a result, however, it was not only impossible to compare the results of different laboratories, but already the same laboratory will, under the same external conditions, obtain different results if the feed-in conditions of the high frequency voltage into the human body are changed by emotional factors of the patient which emotional factors show up in a change of the surface conducting value of the skin.

It is, therefore, an object of the present invention to provide a device which will permit the employment of the Kirlian photography for diagnostic purposes and which will to a major extent eliminate the above mentioned conditions during the feedin of the high frequency energy into the human body.

It is a further object of the present invention to provide a device which will make it possible preferably also to examine by means of the Kirlian photography such areas which cannot only be reproduced but which, according to an extended experience in this field, show signalling effects for disease conditions in the human body.

These and other objects and advantages of the invention will appear more clearly from the following specification in connection with the accompanying drawing, in which:

FIG. 1 diagrammatically illustrates a device according to the invention in a condition for photographing finger tip sparks.

Figure 2:
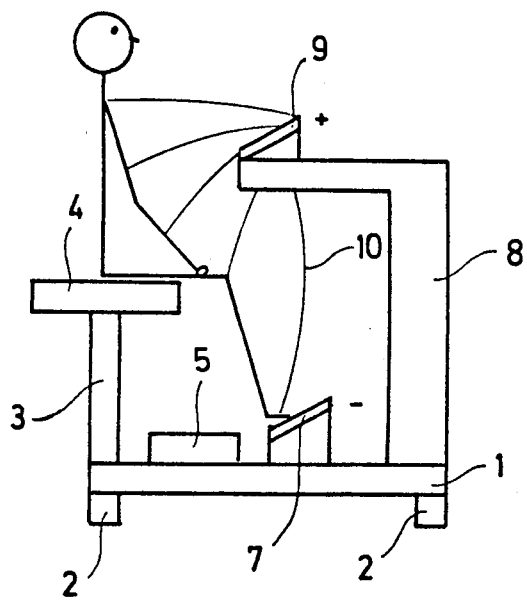

FIG. 2 shows the same device as FIG. 1 but while photographing sparks emanating from the tips of the toes.

The device according to the present invention is characterized primarily by a seating plate insulated relative to the supporting means therefor, a foot plate likewise insulated relative to the supporting means therefor and arranged in front of and below the seating plate, a bottom electrode likewise insulated relative to the supporting means therefor and arranged in spaced relationship ahead of the foot plate, and a plate electrode arranged above the bottom electrode and insulated relative thereto and to the supporting means, while the bottom electrode and the plate electrode are respectively operatively connected to a pole of the high frequency generator.

With this device, the patient can be seated on the insulated seating plate, and when the high frequency generator is connected to the two electrodes, the patient will be seated within an electric field which pulsates between the two electrodes. For taking a picture, the finger tips showing the above mentioned signalling effect are, after the interposition of a light sensitive foil, placed on the plate electrode, while the feet of the patient rest on the insulated foot plate. The introduction or feed-in of the high frequency energy thus is not effected directly into the human body but through the air as dielectricum. As a result thereof, the frequency as well as the pulse frequency and the voltage of the high frequency can be selected within wide limits since these parameters are hardly influenced by a change in the conductivity of the skin or the electric body through the interposed dielectricum. Thus, reproduceable conditions are obtained with regard to the sparks or, according to Kirlian the "high frequency-discharge sparks" which emanate from the finger tips above the sensitive layer of the film. The same applies when the other extreme point, namely the bottom or the tip of the toes having the same signalling effect, is acted upon while the toes are again through the interposition of a light sensitwhich, in contrast to heretofore employed methods, could not be subjectively influenced and which could also not be influenced at will by the patient. Consequently, the present invention makes it possible to precisely diagnose recorded spark phenomena which are recorded by the light sensitive layer of the foil and which can be reproduced at any time in different places with different patients and different evaluating personnel.

Referring now to the drawing in detail, base frame 1 is placed on insulators 2 and this is insulated from the supporting means or from the ground. Arranged on the base frame 1 through an insulator rod 3 is a seating plate 4 which advantageously is likewise insulated or made of insulating material. In front of and below the seating plate 4 there is provided a foot plate or support 5 which is likewise insulated or made of insulating material. In front of the foot plate 5, again on an insulating body 6, is a bottom electrode 7. At the end of an insulating structure 7 and approximately above the bottom electrode 7 there is provided a plate electrode 9. To indicate that the bottom electrode 7 and the plate electode 9 are respectively connected to the two poles of the high frequency generator, the bottom electrode is provided with a minus mark (−) and the plate electrode is provided with a plus sign (+).

When taking a picture of the radiation picture of the finger tips, as will be evident from FIG. 1, the finger tips rest on the plate electrode 9 whereas the foot of the patient rests on the foot plate 5. As a result thereof, the human body is located in an electric field which is indicated by the lines of flux 10.

The introduction of the high frequency energy into the body is effected through the electric field. The same remarks apply when the radiation or spark pictures emanating from the tips of the toes are to be photographed, as shown in FIG. 2. In this connection, merely the tips of the toes rest on the bottom electrode 7, while the plate electrode 9 is not touched. Advantageously, holding means may be provided on the bottom electrode 7 and on the plate electrode 9 for holding film paper. As a result thereof, these papers can always be fed in in the proper position. For instance, after a photograph of the spark picture of the finger tips has been taken on the top side of the film paper, a corresponding photograph of the spark picture emanating from the tip of the toes can be made on the bottom side of the film paper through the bottom electrode 7.

It is, of course, to be understood that the present invention is, by no means, limited to the specific showing in the drawing, but also encompasses any modifications within the scope of the appended claims.

What I claim is:

1. An apparatus for creating pictures reproducable at any time in accurate diagnosis of living conditions with humans by application of Kirlian photography, which includes: a seat, first supporting means for supporting said seat, said seat being insulated with regard to said first supporting means, a foot rest, second supporting means for supporting said foot rest, said foot rest being insulated relative to said second supporting means and being arranged ahead of and at a level below said seat, a bottom electrode, third supporting means for supporting said bottom electrode, said bottom electrode being arranged in spaced relationship to and in front of said foot rest and being insulated relative to sid third supporting means, a plate electrode for holding film paper arranged above said bottom electrode, fourth supporting means for supporting said plate electrode, said plate electrode being arranged above said bottom electrode and being insulated relative to said fourth supporting means, and a HF generator, said bottom electrode and said plate electrode being respectively connected to the poles of said HF generator.

2. An apparatus according to claim 1, which includes a base frame supporting as a unit said seat, said foot rest, said bottom electrode, and said plate electrode, and additional supporting means for supporting said base frame, said base frame being insulated relative to said additional supporting means.

3. An apparatus according to claim 2, in which said bottom electrode and said plate electrode have their top side provided with holding means for holding film paper.

* * * * *